(12) United States Patent
Dhanaraj et al.

(10) Patent No.: US 7,163,920 B2
(45) Date of Patent: Jan. 16, 2007

(54) PEPTIDE WITH OSTEOGENIC ACTIVITY

(75) Inventors: Sridevi Dhanaraj, Raritan, NJ (US);
Anna Gosiewska, Skillman, NJ (US);
Ali Rezania, Hillsborough, NJ (US);
George A. Heavner, Malvern, PA (US);
Xuanhan Lin, Bridgewater, NJ (US);
Chin-Feng Yi, Hillsborough, NJ (US)

(73) Assignee: Ethicon, Inc., Somerville, NJ (US)

( * ) Notice: Subject to any disclaimer, the term of this patent is extended or adjusted under 35 U.S.C. 154(b) by 566 days.

(21) Appl. No.: 10/674,516

(22) Filed: Sep. 30, 2003

(65) Prior Publication Data

US 2005/0187162 A1    Aug. 25, 2005

(51) Int. Cl.
*A61F 2/28* (2006.01)
*A61K 38/08* (2006.01)
*C07K 7/06* (2006.01)

(52) U.S. Cl. ............... 514/16; 424/93.7; 424/423; 514/2; 514/12; 530/300; 530/328; 530/329; 623/23.57; 623/23.6

(58) Field of Classification Search .............. None
See application file for complete search history.

(56) References Cited

U.S. PATENT DOCUMENTS

| | | | |
|---|---|---|---|
| 4,804,744 | A | 2/1989 | Sen |
| 5,013,649 | A | 5/1991 | Wang et al. |
| 5,563,124 | A | 10/1996 | Damien et al. |
| 6,262,017 | B1 | 7/2001 | Dee et al. |

FOREIGN PATENT DOCUMENTS

| | | |
|---|---|---|
| WO | WO 90/05903 | 5/1990 |
| WO | WO 90/11366 | 10/1990 |
| WO | WO 91/05802 | 5/1991 |

OTHER PUBLICATIONS

Szpalski et al.; Applications of Calcium Phosphate-Based Cancellous Bone Void Fillers in Trauma Surgery; Internet Site: www.orthobluejournal.com; pp. 601-609.
Minguell et all; Mesenchymal Stem Cells; Exp Biol Med vol. 226(6); 2001; p. 507-520.
Fibbe; Mesenchymal Stem Cells. A potential source for skeletal repair; Ann Rheum Dis vol. 61 (Suppl II); 2002; pp. 29-31.
Dijkmans et al; Characterization of platelet-derived growth factor-C (PDGF-C): expression in normal and tumor cells, biological activity and chromosomal localization; The International Journal of Biochemistry & Cell Biology vol. 34, 2002; pp. 414-426.
Glowacki et al; The Lancet—Saturday May 2, 1981; The Lancet Ltd, 1981; 959-962.

*Primary Examiner*—Jeffrey Edwin Russel
(74) *Attorney, Agent, or Firm*—Hoffmann & Baron, LLP

(57) ABSTRACT

The present invention provides a composition including an isolated or recombinant peptide component that has osteogenic cell proliferative activity. The peptide, which promotes proliferation of osteoblasts, is useful for treatment of fractures, as a filler in deficient sites of bone, for inhibition of decrease in bone substance related to osteoporosis and periodontic diseases, and for prevention of fractures associated with osteoporosis and rheumatoid arthritis. The peptide, or cells that have been genetically engineered to produce the peptide, can be combined with a bone-compatible matrix to facilitate slow release of the peptide to a treatment site and/or provide a structure for developing bone.

62 Claims, 1 Drawing Sheet

PEPTIDE WITH OSTEOGENIC ACTIVITY

FIELD OF THE INVENTION

The present invention relates to compositions for promoting the production of bone. In particular, the present invention relates to specific osteogenic peptide sequences, which promote the proliferation of osteoblasts, and to implants or devices incorporating these peptides.

BACKGROUND OF THE INVENTION

Mammalian bone tissue has a remarkable ability to regenerate and thereby repair injuries and other defects. Underlying the remodeling process are cells of the osteoblast lineage, which participate in bone formation, and cells of the osteoclast lineage, which participate in bone resorption. These two types of cells are known to originate from distinct early progenitor cells, i.e. stem cells, which differentiate along separate pathways into mature and functional cells, in response to such endogenous mediators as systemic hormones, cytokines and growth factors.

Bone growth is generally sufficient to bring about full recovery for most simple and hairline fractures. Unfortunately, however, there are many injuries, defects or conditions where bone growth is inadequate to achieve an acceptable outcome. For example, bone regeneration generally does not occur throughout large voids or spaces. Therefore, fractures cannot heal unless the pieces are in close proximity. If a significant amount of bone tissue is lost as a result of an injury, the healing process may be incomplete, resulting in undesirable cosmetic and/or mechanical outcomes. This is often the case with non-union fractures or with bone injuries resulting from massive trauma. Tissue growth is also generally inadequate in voids and segmental gaps in bone caused, for example, by surgical removal of tumors or cysts. In other instances, it may be desirable to stimulate bone growth where bone is not normally found, i.e., ectopically. Spine fusion to relieve lower back pain where two or more vertebrae are induced to fuse is one example of desirable ectopic bone formation.

Currently, such gaps or segmental defects require autogenous bone grafts for successful repair or gap filling. The development of effective bone graft substitutes would eliminate the need to harvest bone from a second surgical site for a graft procedure, thereby significantly reducing the discomfort experienced by the patient and risk of donor site healing complications.

Compounds, which stimulate or induce bone growth at sites where such growth would not normally occur if left untreated, are said to be "osteoinductive". Many osteoinductive compounds have been isolated and biochemically identified, and recombinant DNA technologies have been applied to produce relatively large quantities of those having a protein-based structure. These compounds include acidic or basic fibroblast growth factors, platelet-derived growth factor, members of the transforming growth factor superfamily of proteins, insulin-like growth factor, bone morphogenic proteins, etc.

The potential utility of osteogenic proteins has been recognized widely. It is contemplated that the availability of the protein would revolutionize orthopedic medicine, certain types of plastic surgery, and various periodontal and craniofacial reconstructive procedures. However, the use of recombinant proteins as therapeutic agents generally has a number of drawbacks, including the cost of manufacture, in vivo biodegradation, short shelf lives and immunogenicity because of their large molecular weight. Consequently, scientists are continuing to search for new osteoinductive agents, which do not have the aforementioned shortcomings.

A variety of pathological disorders, as well as physical stress (for example, fracture) necessitate active formation of bone tissue at rates that are significantly higher than that which can be supported by the normal milieu of the body. Thus, there is a need in the art to identify physiologically acceptable agents which do not suffer from the disadvantages noted above and which can induce the formation of bone at a predetermined site. Such agents would desirably either provide a permissive matrix structure for the deposition of bone-forming cells or cause growth stimulation of bone-forming cells or induce the differentiation of appropriate progenitors of bone-forming cells.

SUMMARY OF THE INVENTION

Disclosed herein are peptide sequences having osteoblast stimulating activity. In one aspect, the present invention provides an osteoinductive composition comprising an isolated or recombinant peptide component having the formula:

$$R_1\text{-}R_2\text{-}R_3\text{-}R_4\text{-}R_5\text{-}R_6\text{-}R_7\text{-}R_8\text{-}R_9\text{-}R_{10} \quad\quad \text{Formula (I)}$$

or a derivative or a pharmaceutically acceptable salt thereof, wherein:

$R_1$ is H; formyl; mono- or di-lower (C1–C8 linear or branched) alkyl; aryl; lower (C1–C8 linear or branched) alkanoyl; aroyl; aroyl substituted with 1–3 substituents selected from a group consisting of fluorine, chlorine, bromine, C1–C8 linear or branched alkyl, or C1–C8 linear or branched alkyloxy; C1–C8 linear or branched alkyloxycarbonyl; aryloxycarbonyl; or aryloxycarbonyl substituted with 1–3 substituents selected from a group consisting of fluorine, chlorine, bromine, C1–C8 linear or branched alkyl, or C1–C8 linear or branched alkyloxy;

$R_2$ and $R_8$ are each independently selected from D-cysteine, L-cysteine, D-homocysteine, L-homocysteine, D-penicillamine, or L-penicillamine;

$R_3$, $R_4$ and $R_5$ are each glycine; or $R_3$ and $R_4$ taken together are δ-amino-pentanoic acid; or $R_4$ and $R_5$ taken together are δ-amino-pentanoic acid;

$R_6$ is arginine or homo-arginine;

$R_7$ is tryptophan;

$R_9$ is glycine; and $R_{10}$ is OH, C1–C8 linear or branched alkyl ester, lower aryl ester, or $NR_{11}R_{12}$ where $R_{11}$ and $R_{12}$ are each selected independently from H, C1–C8 linear or branched alkyl, or aryl.

Further provided is an osteoinductive implant including: a bone-compatible matrix; and the peptide component of Formula (I); or a derivative or pharmaceutically acceptable salt thereof, wherein the peptide is associated with the bone-compatible matrix.

The present invention also provides a composition including the reaction product of a bone-compatible matrix; osteoinductive cells; and the peptide component of Formula (I), or a derivative or pharmaceutically acceptable salt thereof.

Also provided is a kit that includes one or more containers having a material selected from the following: bone-compatible matrix; carrier or aqueous solvent; stabilizer; preservative; thickener; solubilizer; and cells capable of forming bone. The kit further includes one or more containers including the isolated or recombinant peptide component of Formula (I), or a derivative or pharmaceutically acceptable salt thereof.

Further provided are an isolated or recombinant peptide having SEQ. ID NO: 1 and an isolated DNA sequence encoding the peptide of SEQ. ID NO: 1.

The present invention also provides a method of use for the peptide of Formula (I). In particular, the invention provides a treatment method for promoting the proliferation of osteoblasts. This treatment method includes the step of administering to a patient in need of such treatment an osteoinductive composition including an isolated or recombinant peptide component having Formula (I), or a derivative or a pharmaceutically acceptable salt thereof.

Furthermore, this invention provides a method of preparing an osteoinductive composition which includes the steps of combining a bone-compatible matrix with the peptide component having Formula (I) or a derivative or a pharmaceutically acceptable salt thereof; and immobilizing the peptide component to or within the bone-compatible matrix.

This and other objects of the present invention will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Definitions and Usage of Terms

Figure 1:
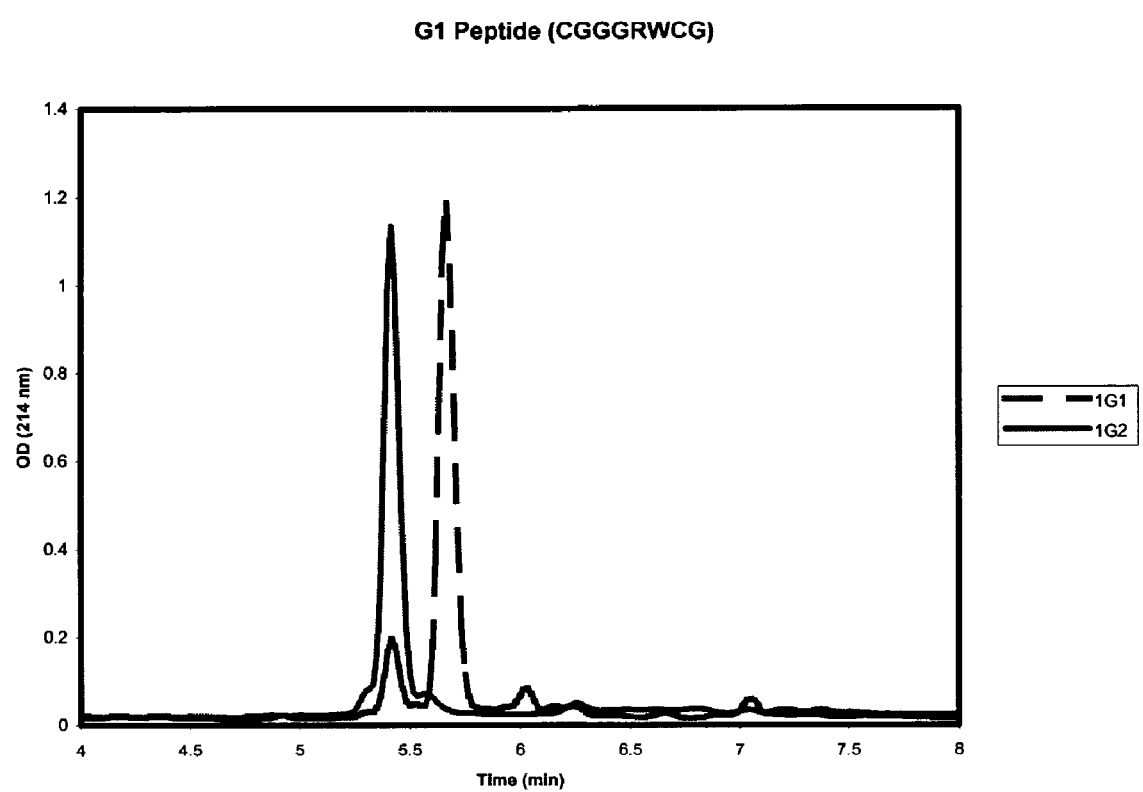
FIG. 1 is a chromatogram of a peptide (SEQ. ID NO: 1) of the present invention prepared in different buffers.

The following definitions and terms are used herein or are otherwise known to a skilled artisan. Except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

Unless otherwise known, stated or shown to be to the contrary, the point of attachment for a multiple term substituent (multiple terms that are combined to identify a single moiety) to a subject structure is through the last named term of the multiple term. For example, a cycloalkylalkyl substituent would attach to a target through the latter "alkyl" portion of the substituent (e.g., Structure-alkyl-cycloalkyl).

The term "substituted," as used herein, means the replacement of one or more atoms or radicals, usually hydrogen atoms, in a given structure with an atom or radical selected from a specified group.

The term "C1–C8 alkyl" as used herein means acyclic, linear or branched chain alkyl substituents containing from 1 to eight carbon atoms and includes, for example, methyl, ethyl, propyl, butyl, tert-butyl, hexyl, 1-methylethyl, 1-methylpropyl, 2-methypropyl, 1,1-dimethylethyl.

The term "C1–C8 alkyloxy" as used herein means the linear or branched radical —O(C1–C8) wherein alkyl is as defined above containing up to eight carbon atoms. Alkyloxy includes, for example, methoxy, ethoxy, propoxy, 1-methylethoxy, butoxy and 1,1-dimethylethoxy. The latter radical is known commonly as tert-butoxy.

The term "C1–C8 alkanoyl" as used herein means linear or branched 1-oxoalkyl radicals containing one to eight carbon atoms and includes, for example, formyl, acetyl, 1-oxopropyl(propionyl), 2-methyl-1-oxopropyl, 1-oxohexyl and the like.

The term "aryl," as used herein, means a substituted or unsubstituted, aromatic, mono- or bicyclic, chemically-feasible carbocyclic ring system having from one to two aromatic rings. The aryl moiety will generally have from 6 to 14 carbon atoms with all available substitutable carbon atoms of the aryl moiety being intended as possible points of attachment. Representative examples include phenyl, tolyl, xylyl, cumenyl, naphthyl, tetrahydronaphthyl, indanyl, indenyl and the like.

The term "chemically-feasible" is usually applied to a ring structure present in a compound and means that the ring structure would be expected to be stable by a skilled artisan.

The term "C1–C8 alkyoxycarbonyl" represents a carboxyl group whose hydrogen atom is substituted by a C1–C8 linear or branched alkyl group as defined herein. A preferable example of the alkoxycarbonyl group is methoxycarbonyl or ethoxycarbonyl group.

The term aryloxycarbonyl represents a carboxyl group whose hydrogen atom is substituted by an aryl group as defined herein. Representative examples include: phenoxycarbonyl, 4-methylphenoxycarbonyl and 4-chlorophenoxycarbonyl.

The term "carbonyl," as used herein, refers to a —C(O)— group.

The term "formyl," as used herein, refers to a —C(O)H group.

The term "aroyl" as used herein, refers to an aryl group, as defined herein, appended to the parent molecular moiety through a carbonyl group, as defined herein. Representative examples of aroyl groups include: benzoyl, cinnamoyl, and naphthoyl.

"Lower aryl," as used herein, is a subset of aryl as defined herein, wherein the substitution on the aryl is a C1–C8 group.

As defined herein, the term "immobilize," "immobilized," and the like is to render the peptide component of the present invention immobile on or within a bone-compatible matrix. The term is intended to encompass passive adsorption of the peptide to the bone-compatible matrix, as well as a direct or indirect covalent or non-covalent attachment of the peptide to the bone-compatible matrix. For example, a direct or indirect covalent bond, ionic bond, hydrophobic bond, hydrogen bond, or sulfur bond can be used to attach the peptide to the matrix. Furthermore, the peptide component can be rendered immobile within the bone-compatible matrix by encapsulating the peptide within the matrix or impregnating the matrix with the peptide.

The term "osteoinductive," "osteogenic," and the like, as used herein, refers to a compound, composition, implant or device which stimulates or induces bone growth at sites where such growth would not normally occur if left untreated.

The term "bone-compatible matrix" as defined herein refers to a delivery vehicle for the peptides of the present invention. The bone-compatible matrix is desirably a porous structure that can be a ceramic, biodegradable polymer, demineralized bone matrix or a combination of these. The matrix can take various forms including, but not limited to, woven or non-woven powder, microparticles, microspheres, microfibers, microfibrils, strip, gel, web, sponge and combinations thereof.

As used herein "osteoblasts" are bone cells that synthesize and excrete the extracellular matrix that forms the structure of bone. Osteoblasts also direct the calcifiation of the bone matrix. The osteoblast is the differentiated product of osteoprogenitor cells.

The terms "mesenchymal stem cells," "osteoprogenitor cells," "osteoprogenitor stem cells," and the like are cells which are found within the bone marrow and exhibit multilineage differentiation capacity. Mesenchymal stem cells can be ex vivo expanded, and induced, either in vitro or in vivo, to terminally differentiate into osteoblasts, chondrocytes, adipocytes, tenocytes, myotubes, neural cells, and hematopoietic-supporting stroma.

The term "isolated" means that the peptide of Formula (I) is essentially free of contaminating peptides or proteins. By "essentially free", it is meant at least 90% free, preferably at least 95% free, and more preferably at least 98% free of contaminating peptides or proteins.

Accordingly, to the present invention, there is provided an osteoinductive composition including an isolated or recombinant peptide component having the formula:

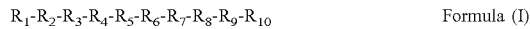

$$R_1\text{-}R_2\text{-}R_3\text{-}R_4\text{-}R_5\text{-}R_6\text{-}R_7\text{-}R_8\text{-}R_9\text{-}R_{10} \quad \text{Formula (I)}$$

or a derivative or a pharmaceutically acceptable salt thereof, wherein:

$R_1$ is H; formyl; mono- or di-lower (C1–C8 linear or branched) alkyl; aryl; lower (C1–C8 linear or branched) alkanoyl; aroyl; aroyl substituted with 1–3 substituents selected from a group consisting of fluorine, chlorine, bromine, C1–C8 linear or branched alkyl, or C1–C8 linear or branched alkyloxy; C1–C8 linear or branched alkyloxycarbonyl; aryloxycarbonyl; or aryloxycarbonyl substituted with 1–3 substituents selected from a group consisting of fluorine, chlorine, bromine, C1–C8 linear or branched alkyl, or C1–C8 linear or branched alkyloxy;

$R_2$ and $R_8$ are each independently selected from D-cysteine, L-cysteine, D-homocysteine, L-homocysteine, D-penicillamine, or L-penicillamine;

$R_3$, $R_4$ and $R_5$ are each glycine; or $R_3$ and $R_4$ taken together are δ-amino-pentanoic acid; or $R_4$ and $R_5$ taken together are δ-amino-pentanoic acid;

$R_6$ is arginine or homo-arginine;

$R_7$ is tryptophan;

$R_9$ is glycine; and $R_{10}$ is OH, C1–C8 linear or branched alkyl ester, lower aryl ester, or $NR_{11}R_{12}$ where $R_{11}$ and $R_{12}$ are each selected independently from H, C1–C8 linear or branched alkyl, or aryl.

In one desired embodiment, the peptide for use in the osteoinductive composition has the amino acid sequence represented by Cys-Gly-Gly-Gly-Arg-Trp-Cys-Gly (SEQ. ID NO: 1).

Homologs of the peptide of Formula (I) are further included within the scope of the present invention. A homolog can be, for example, a substitution, addition, or deletion mutant of the peptide. For example, it is preferred to substitute amino acids in a sequence with equivalent amino acids. Groups of amino acids known normally to be equivalent are:

(a) Ala(A), Ser(S), Thr(T), Pro(P), Gly(G);
(b) Asn(N), Asp(D), Glu(E), Gln(Q);
(c) His(H), Arg(R), Lys(K);
(d) Met(M), Leu(L), Ile(I), Val(V); and
(e) Phe(F), Tyr(Y), Trp(W).

Substitutions, additions, and/or deletions in an amino acid sequence can be made by a usual technique in genetic engineering or in peptide synthesis as long as the peptide homolog continues to have osteogenic activity. An amino acid sequence that is substantially the same as another sequence, but that differs from the other sequence by means of one or more substitutions, additions, and/or deletions, is considered to be an equivalent sequence. Preferably, less then 50%, more preferably less than 25%, and still more preferably less than 10%, of the number of amino acid residues in the peptide sequence are substituted for, added to, or deleted from the peptide.

It is noted that unless indicated otherwise, peptide forms of this invention include peptides represented by Formula (I), such as the peptide having SEQ. ID NO 1, as well as derivatives, thereof. For example, the peptide of Formula (I) may form a part of a longer peptide or polypeptide. Moreover, fragments or mutants of the peptide of Formula (I) are encompassed by the present invention. Furthermore, this invention encompasses a family of related proteins or truncated forms thereof having regions of amino acid homology with the peptide of Formula (I). These may be naturally occurring or biosynthetically derived. The present invention also includes all relevant nucleotide sequences encoding a peptide of Formula (I), or its derivatives. For example, the present invention provides an isolated DNA sequence encoding the peptide of SEQ. ID NO 1.

The amino acid substitutions presented in the present specification are designed to have minimal impact on the peptide. For example, substituted cysteines (e.g., penicillamine-β, β-dimethyl cysteine) in Formula (I) will stabilize backbone structures in cyclic disulfide peptides. Substitutions such as homo-arginine for arginine (the addition of a methylene group that increases the length of the side chain) are expected to result in retention of osteogenic activity. These and the other amino acid substitutions presented herein were rationally designed so as to have minimal impact on the backbone conformation, the conformation of the amino acid side chains and the electron density of both side chains and backbone. Therefore, peptides resulting from these substitutions should be functional analogs of the peptide represented by SEQ. ID NO: 1. Similarly, deleted or added amino acids may be selected as appropriate depending on the type of amino acids, site and the like.

In the present specification, "osteogenic activity" may be construed as enhancing the expression of alkaline phosphatase in osteoblasts so as to form neogenetic bone or induce growth of existing bone. The peptide of the present invention has osteogenic activity and is negligible in toxicity, such as cytotoxity, since the peptide stimulated proliferation of osteoblasts.

In the present specification, amino acid residues are represented by abbreviatory symbols as follows:

Cys: L-cysteine residue (C)
Gly: L-glycine residue (G)
Arg: L-arginine residue (R)
Trp: L-tryptophane residue (W)

Also in the present specification, the amino acid sequence of a peptide is written according to the conventional notation, with an amino group at the N-terminal appearing on the left hand of the sequence and carboxyl group at the C-terminal appearing on the right hand thereof.

Peptides, defined as consisting of between four and one hundred amino acids, having osteogenic activity, therapeutic compositions containing these peptides, methods for preparation of these peptides and methods of use thereof are disclosed herein.

The peptide of the present invention may form a physiologically acceptable salt by conventional salt formation reaction. Such salts can include salts with inorganic acids such as hydrochloric acid, sulfuric acid and phosphoric acid; salts with organic acids such as lactic acid, tartaric acid, maleic acid, fumaric acid, oxalic acid, malic acid, citric acid, oleic acid and palmitic acid; salts with hydroxides and carbonates of alkali metals and alkali earth metals such as sodium, potassium, calcium and aluminum; and salts with amines such as triethylamine, benzylamine, diethanolamine, t-butylamine, dicyclohexylamine and arginine.

As described in further detail below, in one embodiment, the peptides of the present invention are chemically synthesized. In other embodiments, the peptides of the present invention are produced in vivo or ex vivo by expression of recombinant DNA in procaryotic or eukaryotic host cells.

Both inter- and intra-chain disulfide bonds may be formed and the present invention encompasses peptide forms resulting from the formation of such disulfide bonds. Disulfide linkages can form between the monomeric strands of the peptides. This may occur between one Cys on each strand. Disulfide linkages may form between two Cys on each peptide. Various homodimers having the same peptide component strands may form with different numbers of disulfide linkages. Various homodimers having the same peptide component strands may form with disulfide bonds at different Cys locations. Different homodimers encompassed by this invention having the same peptide components may differ based upon their recombinant production in mammalian cells, bacterial cells, insect, or yeast cells. In one embodiment of the present invention, the osteoinductive composition of the present invention includes a homodimer of the peptide component having Formula (I).

The peptide of the present invention may be used singly in the osteoinductive composition for the purpose of preventing or treating bone fractures. Also, the peptide may be used in the form of an osteogenetic accelerator obtained by fixing, mixing, dissolving or suspending the peptide in a pharmaceutically acceptable carrier or an aqueous solvent. For example, suitable examples of carriers or aqueous solvents include, but are not limited to, clinical grade sterile water, sterile saline, sterile buffered saline, dextrose in sterile water, sterile liquid media or other physiologically acceptable isotonic liquids. The osteoinductive composition of the present invention can contain a variety of pharmacologically acceptable additives, such as a stabilizer, a preservative, a thickener, a solubilizer and the like, which can be combined with the carrier or aqueous solvent.

The peptide of the present invention can be useful in clinical applications in conjunction with a suitable matrix that acts as a delivery or support system. A successful matrix for an osteogenic peptide desirably performs several important functions. It desirably binds the osteogenic peptide and acts as a slow release delivery system, accommodates each step of the cellular response during bone development, and protects the osteogenic peptide from nonspecific proteolysis. In addition, selected materials should be biocompatible in vivo, porous and preferably biodegradable. In bones, the dissolution rates can vary according to whether the implant is placed in cortical or trabecular bone. The matrix desirably also acts as a temporary scaffold until replaced by new bone formation. Therefore, in one embodiment, the bone-compatible matrix provides for slow release of the peptide component to a patient in need of the osteoinductive composition and/or provides a structure for developing bone in the patient.

It is noted that it is also well within the contemplation of the present invention that cells that have been genetically engineered to contain a nucleic acid sequence encoding a peptide of the present invention can be incorporated into the matrix for in vivo production of the peptide at the treatment site.

The matrix is preferably selected from a ceramic, a biodegradable biopolymer, demineralized bone matrix, and combinations thereof. In one embodiment, the bone-compatible matrix is a woven or non-woven porous structure. In another embodiment, the bone-compatible matrix is in a form selected from the following: powder, microparticles, microspheres, microfibers, microfibrils, strip, gel, web, sponge, and combinations thereof.

Suitable ceramics for use as a bone-compatible matrix include, but are not limited to, calcium sulfate, hydroxyapatite, tricalcium phosphate, as well as combinations thereof. Other ceramics used as artificial bone are also suitable. The ceramic can be in particulate form or can be in the form of a structurally stable, three-dimensional implant (e.g., a scaffold). The implant can be, for example, a cube, cylinder, block or an appropriate anatomical form.

The bone-compatible matrix may be comprised of natural, modified natural or synthetic biodegradable polymers, copolymers, block polymers, as well as combinations thereof. It is noted that a polymer is generally named based on the monomer it is synthesized from. Examples of suitable biodegradable polymers or polymer classes include fibrin, collagen, elastin, celluloses, gelatin, vitronectin, fibronectin, laminin, reconstituted basement membrane matrices, starches, dextrans, alginates, hyaluron, chitin, chitosan, agarose, polysaccharides, hyaluronic acid, poly(lactic acid), poly(glycolic acid), polyethylene glycol, decellularized tissue, self-assembling peptides, polypeptides, glycosaminoglycans, their derivatives and mixtures thereof. For both glycolic acid and lactic acid, an intermediate cyclic dimer is typically prepared and purified, prior to polymerization. These intermediate dimers are called glycolide and lactide, respectively. Self-assembling peptides are described in U.S. Pat. Nos. 5,670,483 and 5,955,343.

Other useful biodegradable polymers or polymer classes include the following: polydioxanones, polycarbonates, polyoxalates, poly($\alpha$-esters), polyanhydrides, polyacetates, polycaprolactones, poly(orthoesters), polyamino acids, polyamides and mixtures and copolymers thereof.

Additional useful biodegradable polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of $\alpha$-amino acids, copolymers of $\alpha$-amino acids and caproic acid, copolymers of $\alpha$-benzyl glutamate and polyethylene glycol, copolymers of succinate and poly(glycols), polyphosphazene, polyhydroxy-alkanoates and mixtures thereof. Binary and ternary systems are contemplated.

Other specific biodegradable polymers which are useful include those marketed under the Biodel and Medisorb trademarks. The Biodel materials represent a family of various polyanhydrides which differ chemically. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100/0, believed to be 100% lactide having a melting point within the range of 338°–347° F. (170°–175° C.); lactide/glycolide 0/100, believed to be 100% glycolide having a melting point within the range of 437°–455° F. (225°–235° C.); lactide/glycolide 85/15, believed to be 85% lactide and 15% glycolide with a melting point within the range of 338°–347° F. (170°–175° C.); and lactide/glycolide 50/50, believed to be a copolymer of 50% lactide and 50% glycolide with a melting point within the range of 338°–347° F. (170°–175° C.).

In one desirable aspect of the invention, the polymer used to form the bone-compatible matrix is a hydrogel. More desirably, the hydrogel is produced from a synthetic polymeric material. Such synthetic polymers can be tailored to a range of properties and predictable lot-to-lot uniformity, and represent a reliable source of material and one generally free from concerns of immunogenicity. In general, hydrogels are polymeric materials that can absorb more than 20% of their weight in water while maintaining a distinct three-dimensional structure. This definition includes dry polymers that will swell in aqueous environments, as well as to water-swollen materials. A host of hydrophilic polymers can be cross-linked to produce hydrogels, whether the polymer is of biological origin, semi-synthetic, or wholly synthetic.

In general, a suitable biodegradable polymer for use as the bone-compatible matrix is desirably configured so that it has mechanical properties that match the application, remaining sufficiently intact until bone tissue has in-grown and healed, does not invoke an inflammatory or toxic response, is metabolized in the body after fulfilling its purpose, leaving no trace, is easily processible into the final product formed, demonstrates acceptable shelf-life, and is easily sterilized.

Properties that make hydrogels valuable in drug delivery applications include the equilibrium swelling degree, sorption kinetics, solute permeability, and their in vivo performance characteristics. Permeability to compounds, including the peptide of Formula (I), depends in part upon the swelling degree or water content and the rate of biodegradation. Since the mechanical strength of a gel declines in direct proportion to the swelling degree, it is also well within the contemplation of the present invention that the hydrogel can be attached to a substrate so that the composite system enhances mechanical strength. In alternative embodiments, the hydrogel can be impregnated within a porous substrate, such as a ceramic scaffold, so as to gain the mechanical strength of the substrate, along with the useful delivery properties of the hydrogel for the peptide of Formula (I).

Factors affecting the mechanical performance of in vivo biodegradable polymers are well known to the polymer scientist, and include monomer selection, initial process conditions, and the presence of additives. Biodegradation has been accomplished by synthesizing polymers that have unstable linkages in the backbone, or linkages that can be safely oxidized or hydrolyzed in the body. The most common chemical functional groups having this characteristic are ethers, esters, anhydrides, orthoesters and amides. Therefore, in one embodiment of the present invention, the peptide component is controllably released from the biodegradable polymer to the site where it is needed by hydrolysis of chemical bonds in the biodegradable polymer. Biodegradable polymers are preferably in the form of a powder, microparticle, microsphere, strip, gel, web or sponge.

As described above, the bone-compatible matrix can be a demineralized bone matrix (DBM). This is produced by decalcifying cortical bone, and represents a form of allograft processing (Trumees, E. and Herkowitz, H. (1999) Univ. of Penn. Orthop. J. 12:77–88). The resulting matrix is more osteoinductive than ordinary allograft. One commercially available preparation of a demineralized bone matrix gel is Grafton gel (Osteotech, Inc., Eatontown, J), which combines DBM with a glycerol carrier.

The matrix medium, vehicle excipient or carrier can be any of those known to be pharmaceutically acceptable for administration to a patient, particularly locally at the site at which new bone growth is to be induced. Examples include liquid media, for example, Dulbeccos Modified Eagles Medium (DMEM), sterile saline, dextrose in sterile water and any other physiologically acceptable isotonic liquid.

In one embodiment, one or more of the peptides of the present invention is immobilized to the bone-compatible matrix. In another embodiment, one or more of the inventive peptides is impregnated or encapsulated within the bone-compatible matrix so as to be immobilized therewithin. Furthermore, cells which have been genetically engineered to include a nucleic acid sequence encoding a peptide of the present invention can be impregnated or encapsulated within the bone-compatible matrix so as to produce the peptide at the treatment site.

As discussed above, one or more of the peptides represented by Formula (1) can be impregnated within a porous bone-compatible matrix. For example, it is contemplated that the peptide of Formula (I) may be blended with a fluid material such as an aqueous solvent or a hydrogel to form a mixture which is used to impregnate the pores of a porous bone-compatible matrix, such as a ceramic scaffold. Alternatively, it is contemplated that the pores of the bone-compatible matrix may first be filled with a fluid material and that air pressure or other suitable means may then be employed to disperse a dry peptide of this invention substantially evenly within the filled pores of the bone-compatible matrix.

In a further embodiment, the peptide may be encapsulated in a polymer or a lipid-containing vesicle, such as a liposome, so as to allow for a controlled release of the peptide to a site where it is needed. For example, the polymeric matrix containing one or more peptides according to the present invention may include, without limitation, microparticles, microspheres, microfibers or microfibrils. In one example, a microsphere could be contained within a mesh of a polymeric scaffold or other implant or device for peptide delivery. The microspheres containing the peptide may be incorporated within a polymeric scaffold by adhesively positioning them onto the scaffold. Alternatively, microspheres may be mixed with a fluid or gel and allowed to flow into the polymeric matrix of the scaffold. Moreover, microfibers or microfibrils, which may be peptide loaded by extrusion, can be adhesively layered or woven into the polymeric material included in a surface of a scaffold for peptide delivery.

As described above, it is contemplated that one or more peptides according to the present invention can be encapsulated within a liposome. Liposomes are spherical vesicles prepared from either natural or synthetic phospholipids or cholesterol. These vesicles can be composed of either one (unilamellar liposomes) or several (oligo- or multilamallar liposomes) lipid bilayes surrounding internal aqueous volumes. It is known to entrap drugs, proteins and nucleic acids within the internal aqueous space of a liposome. For example, U.S. Pat. No. 5,567,433 discloses a liposome preparation including encapsulated granulocyte-colony stimulating factor (G-CSF), a relatively unstable protein. In addition, U.S. Pat. No. 4,241,046 describes a method for encapsulating an enzyme within a synthetic liposome, the product liposomes being useful for enzyme replacement therapy. Liposomes allow the parenteral administration of the therapeutic agent. On the cellular level, liposomes interact with cell membranes by adsorption, endocytose, membrane fusion, and lipid exchange, or by a combination of these mechanisms as described by Pagano and Weinstein in Ann. Rev. Biophys. Bioeng. (1978) 7:435. Fast elimination of the therapeutic agent and its metabolism can be impeded by shielding the therapeutic agent in a liposome. See, for example, Schwendener, et al., Biochim. Biophys. Acta (1990) 1026:69–79 and Schwendener (1992) Chimia 46:69–77.

It is well within the contemplation of the present invention that one or more of the inventive peptides can be combined with a variety of orthopedic devices, including, but not limited to, bone graft material, replacement knees, hips, joints, pins, rods, plates, screws, fasteners, darts, arrows and staples.

There are many methods of immobilizing the peptide to a bone-compatible matrix. It is possible to adopt an immobilization method allowing formation of a covalent bond, ionic bond, hydrophobic bond, hydrogen bond, sulfur-sulfur bond or the like, for example, an immersion, impregnation, spray, application and dropping method with use of a solution containing the peptide. Among these immobilization methods, fixation by covalent bond is preferred from the viewpoint of stability and continuity of effect. Such fixation can be done by a method usually used for fixing a physiologically active protein such as an enzyme.

For example, in one embodiment, free carboxyl groups on a biocompatible, biodegradable polymer forming the bone-compatible matrix may be chemically cross-linked to a free amino group on the peptide using carbodiimide as a cross-linker agent. Other standard immobilization chemistries are known by those of skill in the art and can be used to join the peptides of the present invention to the bone-compatible matrix. For example, see *Protein Immobilization: Fundamentals and Applications* Taylor, R. (Ed.) M. Dekker, NY, (1991).

Preferably, the peptide to be immobilized is used in an amount of about 0.01 to about 50 parts by weight, preferably about 0.1 to 25 parts by weight, with respect to 100 parts by weight of a dry bone-compatible matrix material, such as hydroxyapatite. The peptide thus immobilized is usually used for treatment of a fracture or the like by being implanted in a deficient site in bone. If the peptide is used in an amount smaller than 0.01 parts by weight with respect to 100 parts by weight of a dry bone-compatible matrix material, the effect of the peptide tends to be insufficient. If the peptide is used in an amount larger than 50 parts by weight, on the other hand, the ratio of fixation of the peptide to the bone-compatible matrix declines and the peptide tends not to be utilized effectively.

The therapeutic method of the present invention includes administering the inventive peptide composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than the peptide of the current invention, which may also optionally be included in the inventive peptide composition as described above, may alternatively or additionally, be administered simultaneously or sequentially with the peptide composition in the methods of the invention. The dose of the peptide as an active ingredient may vary as required depending upon the weight of bone desired to be formed, the site of injured bone, the condition of bone, and the age, sex and weight of a patient and the like.

The peptide can also be administered in combination with additional components, such as osteoinductive factors. The osteoinductive factors include any that are now known and any factors which are later recognized to have osteoinductive activity. Such osteoinductive factors include, for example, dexamethasone, ascorbic acid-2-phosphate, beta-glycerophosphate and combinations thereof. The composition can also contain antibiotic, antimycotic, antiinflammatory, immunosuppressive and other types of therapeutic, preservative and excipient agents.

Furthermore, the peptide can be administered in combination with an osteoinductive substance selected from the following: growth factors, cytokines, hormones, enzymes, enzyme inhibitors, bone matrix components, growth differentiation factors and combinations thereof.

It is expected that the proteins of the invention may act in concert with other related proteins and growth factors. These agents include various growth factors such as epidermal growth factor (EGF), platelet derived growth factor (PDGF), members of the transforming growth factor superfamily of proteins (e.g., TGF-α and TGF-β), insulin-like growth factor (IGF), basic fibroblast growth factor (bFGF), bone morphogenic proteins (BMPs) and combinations thereof.

For example, the following molecules have a mitogenic effect and are polypeptides that exhibit heparin-binding affinity: acidic fibroblast growth factor, basic fibroblast growth factor, platelet-derived growth factor, and an insulin-like growth factor II, originally called skeletal growth factor. Moreover, it has been demonstrated that TGF-$\beta_2$ is effective in promoting bone mass in several animal models. Furthermore, BMPs are members of the transforming growth factor (TGF) P family. BMP has the function of acting on undifferentiated mesenchymal cells, inducing differentiation to chondroblasts and osteoblasts and effecting chondrogenesis and osteogenesis. Moreover, BMPs are characterized by the presence of several interchain disulfide bonds essential to bioactivity (they exist as a homodimer in their active form) and moderate affinity for heparin.

The osteogenic peptide disclosed herein will permit the physician to obtain optimal predictable bone formation to correct, for example, acquired and congenital craniofacial and other skeletal or dental anomalies (Glowacki et al. (1981) Lancet 1: 959–963). The devices may be used to induce local endochondral bone formation in non-union fractures as demonstrated in animal tests, and in other clinical applications including dental and periodontal applications where bone formation is required. Another potential clinical application is in cartilage repair, for example, in the treatment of osteoarthritis.

Thus, the peptides of the present invention, either alone or in combination with a pharmaceutically acceptable carrier, implant or device can promote treatment of fractures by being administered to patients with fractures caused by rheumatoid arthritis and osteoporosis or by being filled or implanted in a defective site in bone. Also, they can inhibit a decrease in bone substance and prevent fractures by being administered to patients with rheumatoid arthritis, osteoporosis and periodontic diseases.

In view of the disclosure made herein, and using standard methodologies known in the art, persons skilled in the art can raise polyclonal and monoclonal antibodies against all or part of peptides of the present invention, such that the antibodies are capable of binding specifically to an epitope on the peptide chain. The antibodies could be useful in monitoring levels of the peptide during therapy. This is discussed in further detail below.

Another aspect of the invention provides a method for accelerating the rate of differentiation of human mesenchymal stem cells using one or more of the peptides of the present invention.

Mesenchymal stem cell (MSC) therapy can serve as a means to deliver high densities of repair-competent cells to a defect site when adequate numbers of MSC and MSC lineage-specific cells are not present in vivo, especially in older and/or diseased patients. In order to efficiently deliver high densities of MSC to a defect site, methods for rapidly producing large numbers of MSC are necessary. Methods that increase the ex vivo proliferation rate of MSC will greatly increase the utility of MSC therapy. Similarly, methods that increase in vivo proliferation rate of MSC will enhance the utility of MSC therapy by rapidly increasing local concentrations of MSC at the repair site. Furthermore, methods that enhance the proliferation rate of lineage-specific descendants of MSC, including, but not limited to, bone marrow stromal cells, osteoclasts, chondrocytes, and adipocytes, will enhance the therapeutic utility of MSC therapy by increasing the concentration of lineage-specific cell types at appropriate repair sites.

Osteogenesis (i.e., the production of new bone) can occur directly from osteoblasts and osteoprognitor cells. For example, circulating mesenchymal stem cells and osteoinductive growth factors can migrate and adhere to a bone-compatible matrix, such as a ceramic scaffold, in the body. Within the scaffold, progenitor cells can differentiate into functioning osteoblasts. In one embodiment of the present invention, an orthopedic implant or device is provided which includes one or more of the peptides of the present invention, and which also includes osteogenic cells, such as osteoprogenitor stem cells and/or osteoblasts so as to increase the osteoinductive potential associated with bone-graft substituents like ceramic scaffolds. Mesenchymal stem cells are described by Minguell, J., et al. (2001) Exp. Biol. Med 226(6); 507–520 and by Fibbe, W. (2002) Ann Rheum Dis 61 (Suppl II): ii29–ii31. It is within the contemplation of the present invention that these cells can be incorporated into an implant or device prior to, during, or following implantation. The implant or device may further incorporate other osteoinductive substances, such as those described herein.

The therapeutic compositions of the present invention may also be used for veterinary applications. Particularly domestic animals and thoroughbred horses, in addition to humans, are desired patients for such treatment with peptide of the present invention.

Preparation of Peptide

The peptides of the present invention may be prepared by methods known in the art. Such methods include synthesizing the protein chemically from individual amino acids or synthesizing DNA encoding the peptide and using the DNA to produce recombinant peptide ex vivo or in vivo.

A. Chemical Synthesis of Peptide

The peptide of the invention and DNA encoding the peptide may be chemically synthesized by methods known in the art. Suitable methods for synthesizing the peptide are described by Stuart and Young (1984), "Solid Phase Peptide Synthesis," *Solid Phase Peptide Synthesis, Methods Enzymol.*, Second Edition, Pierce Chemical Company, 289, Academic Press, Inc., NY (1997).

For example, a solid phase synthesis method or a liquid phase synthesis method may be used. The solid phase synthesis is usually carried out by protecting amino groups with appropriate protecting groups. For example, either Boc (tert-butoxycarbonyl) or Fmoc (9-fluorenylmethyloxycarbonyl), or a combination thereof may be used.

One example of fabricating the peptide of the present invention is to follow the following steps:

1) an amino acid corresponding to the C-terminal of the peptide to be produced is bonded to a solid phase material insoluble to a reaction solvent via an α-COOH group of the amino acid;
2) in the direction towards the N-terminal of the peptide, a corresponding amino acid or peptide fragment is bonded by condensation to the amino acid of step 1) after protecting other functional groups such as an α-amino group of the corresponding amino acid or peptide fragment other than an α-COOH group;
3) a protecting group of an amino group forming a peptide bond such as an α-amino group is removed from the bonded amino acid or peptide fragment;
4) steps 2) and 3) are repeated to elongate a peptide chain in order to form a peptide chain corresponding to the desired peptide;
5) detach the produced peptide chain is from the solid phase material and remove the protecting groups from the protected functional groups; and
6) the peptide chain is purified, thereby to obtain the desired peptide.

Here, as the solid phase material, styrene-divinyl benzene copolymers, polyethylene glycol polymers, Merrifield resins, chloromethyl resins, Wang resins, Sieber resins, rink amide resins, rink acid resins, 2-chlorotrityl chloride resins, HMBA-MBHA resins, MBHA resins, oxime resins and the like may be used. Among these resins, styrene-divinyl benzene copolymers are preferred.

As a solvent and a condensing agent in the peptide synthesis, any of those usually known in the art may be used as required. For example, DMF (dimethylformamide), trifluoroethanol, N-methylpyrrolidone and the like may be mentioned as solvents, DCC(Dicyclohexylcarbodiimide), HATU (O-(7-azabenzotriazole-1-yl)-1,1,3,3-tetramethyl uronium hexafluorophosphate), HOBt (1-hydroxybenzotriazole), HBTU (O-Benzotriazolyl-N,N,N', N'-tetramethyluronium hexafluorophosphate), PyBOP (Benzotriazol-1-yloxytripyrrolidinophosphonium hexafluorophosphate), CF3-NO2-PyBOP [1-hydroxy-4-nitro-6-(trifluoromethyl)-1H-benzotriazolato-O1]tri-1-pyrrolidinyl-hexafluorophosphate, and the like may be mentioned as condensing agents.

For purifying the obtained peptide, it is effective to utilize reverse phase liquid chromatography, ion exchange chromatography, hydrophobic interaction chromatography, partition chromatography, counter current distribution or other similar techniques. Either or both of the N- and C-terminals of the peptide of the present invention may optionally be modified chemically. For example, the N-terminal may be acetylated and the C-terminal may be amidated.

B. Chemical Synthesis and Expression of DNA

The DNA encoding the peptide of the invention may be replicated and used to express recombinant peptide following insertion into a wide variety of host cells in a wide variety of cloning and expression vectors. The host may be prokaryotic or eukaryotic. The DNA may be chemically synthesized. Suitable methods for synthesizing DNA are described by Caruthers in Science (1985) 230:281–285 and *DNA Structure, Part A: Synthesis and Physical Analysis of DNA*, Lilley. D. and Dahlberg, J. (Eds.). *Methods Enzymol.*, 211, Academic Press, Inc., NY (1992).

Cloning vectors may comprise segments of chromosomal, non-chromosomal and synthetic DNA sequences. Some suitable prokaryotic cloning vectors include plasmids from *E. coli*, such as colE1, pCR1, pBR322B9, pUC, pKSM, and RP4. Prokaryotic vectors also include derivatives of phage DNA such as M13 fd, and other filamentous single-stranded DNA phages.

Vectors for expressing proteins in bacteria, especially *E. coli*, are also known. Such vectors include the pK233 (or any of the tac family of plasmids), T7, pBluescript II, bacteriophage lamba ZAP, and lambda $P_L$. For example, see *Recombinant DNA Methodology II, Methods Enzymol.*, Wu, R. (Ed.), Academic Press, Inc., NY, (1995). Examples of vectors that express fusion proteins are PATH vectors described by Dieckmann and Tzagoloff (1985) J. Biol. Chem. 260:1513–1520. These vectors contain DNA sequences that encode anthranilate synthetase (TrpE) followed by a polylinker at the carboxy terminus. Other expression vector systems are based on β-galactosidase (pEX); maltose binding protein (pMAL); glutathione S-transferase (pGST or PGEX) (Smith, D (1993) Methods Mol. Cell Biol. 4:220–229; Smith, D. and Johnson, K. (1988) Gene 67:31–40; and Peptide Res. (1990) 3:167; and TRX (thioredoxin) fusion protein (LaVallie, R., et al. (1993) Bio/Technology 11:187–193).

Vectors useful for cloning and expression in yeast are available. Suitable examples are 2 μm circle plasmid, Yep50, Yep24, Yrp7, Yip5, and pYAC3. See for example, *Current Protocols in Molecular Biology*. Ausubel, F. M. et al., (Eds.) John Wiley & Sons, NY (1999).

Suitable cloning/expression vectors for use in mammalian cells are also known. Such vectors include well-known derivatives of SV-40, adenovirus, cytomegalovirus (CMV) retrovirus-derived DNA sequences. Any such vectors, when coupled with vectors derived from a combination of plasmids and phage DNA, i.e. shuttle vectors, allow for the isolation and identification of amino acid coding sequences in prokaryotes.

Further eukaryotic expression vectors are known in the art (e.g., Southern, P. and Berg, P. (1982) Mol. Appl. Genet. 1:327–341; Subramani, S., et al. (1981) Mol. Cell. Biol. 1:854–864; Kaufmann, R. and Sharp, P. (1982) J. Mol. Biol. 159:601–621; Kaufmann, R. and Sharp, P. (1982) Mol. Cell. Biol. 159:601–664; Scahill, S., et al. (1983) Proc. Natl. Acad. Sci. USA 80:4654–4659; Urlaub, G. and Chasin, L. (1980) Natl. Acad. Sci. USA 77:4216–4220.

The expression vectors useful in the present invention contain at least one expression control sequence that is operatively linked to the DNA sequence or fragment to be expressed. The control sequence is inserted in the vector in order to control and regulate the expression of the cloned DNA sequence. Examples of useful expression control sequences are the lac system, the trp system, the tac system, the trc system, the tet system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast α-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Useful expression hosts include well-known prokaryotic and eukaryotic cells. Some suitable prokaryotic hosts include, for example, *E. coli*, such as *E. Coli* SG-936, *E. coli* HB 101, *E. coli* W3110, *E. coli* X1776, *E. coli* X2282, *E. coli* DH1, *E. coli* DH5aF', and *E. coli* MRC1, *Pseudomonas, Bacilus*, such as *Bacillus subtilis*, and *Streptomyces*. Suitable eukaryotic cells include yeasts and other fungi, insect, animal cells, such as COS cells and CHO cells, human cells and plant cells in tissue culture.

The recombinant peptide, which can be expressed in the form of a fusion protein, is purified by methods known in the art. Such methods include affinity chromatography using specific antibodies. Alternatively, the recombinant protein may be purified using a combination of ion-exchange, size-exclusion, hydrophobic interaction chromatography and reverse phase liquid chromatography using methods known in the art. These and other suitable methods are described by Marston, "The Purification of Eukaryotic Proteins Expressed in *E. coli*" *DNA Cloning*, D. Glover (Ed.), Volume III, IRL Press Ltd., England (1987); "Guide to Protein Purification", M. Deutscher (Ed.), *Methods Enzymol.*, Academic Press, Inc., (Ed.), NY (1990); and *Protein Purification*, Scopes, R. and Cantor, C. (Eds.), (3d), Springer-Verlag, NY (1994).

C. Fusion Proteins

The peptides of the invention may be expressed in the form of a fusion protein with an appropriate fusion partner. The fusion partner preferably facilitates purification and identification. Increased yields may be achieved when the fusion partner is expressed naturally in the host cell. Some useful fusion partners include β-galactosidase (Gray, et al. (1982) Proc. Natl. Acad. Sci. USA, 79:6598); trpE (Itakura, et al. (1977) Science 198:1056); protein A (Uhlen, et al. (1983) Gene 23:369; glutathione S-transferace (Smith, D. (1993) Methods Mol. Cell Biol. 4:220–229; Smith, D. and Johnson, K. (1988) Gene 67:31–40; Van Etten, et al. (1989) Cell 58:669; and maltose-binding protein (Guan, et al., (1987) Gene 67:21–30; Maina, et al. (1988) Gene 74:36–373 and *Current Protocols in Molecular Biology*, Ausubel, F., et al., (Eds.), John Wiley & Sons, Inc., NY (1990).

Such fusion proteins may be purified by affinity chromatography using reagents that bind to the fusion partner. The reagent may be a specific ligand of the fusion partner or an antibody, preferably a monoclonal antibody. For example, fusion proteins containing β-galactosidase may be purified by affinity chromatography using an anti-β-galactosidase antibody column (Ullman (1984) Gene 29:27–31). Similarly, fusion proteins containing maltose binding protein may be purified by affinity chromatography using a column containing cross-linked amylase; see Guan, European Patent Application 286,239.

The peptide may occur at the amino-terminal or the carboxy-terminal side of the cleavage site. Optionally, the DNA that encodes the fusion protein is engineered so that the fusion protein contains a cleavable site between the protein and the fusion partner. Both chemical and enzymatic cleavable sites are known in the art. Suitable examples of sites that are cleavable enzymatically include sites that are specifically recognized and cleaved by collagenase (Keil, et al. (1975) FEBS Letters 56:292–296; enterokinase (Prickett, K., et al. (1989) Biotechniques 7:580–589; LaVallie, et al. (1993) J. Biol. Chem. 268:23311–23317); factor Xa (Nagai, et al. (1987) Methods Enzymol. 153:461–481); and thrombin (Eaton, et al. (1986) Biochemistry 25:505 and Chang, J. (1985) Eur. J. Biochem. 15 1:217–224). Collagenase cleaves between praline and X in the sequence Pro-X-Gly-Pro wherein X is a neutral amino acid. Enterokinase cleaves after lysine in the sequence Asp-Asp-Asp-Asp-Lys (SEQ ID NO:2). Factor Xa cleaves after arginine in the sequence Ile-Glu (SEQ ID NO:3) or Asp-Gly-Arg (SEQ ID NO:4).

Thrombin cleaves between arginine and glycine in the sequence Arg-Gly-Ser-Pro (SEQ ID NO:5).

Specific chemical cleavage agents are also known. For example, cyanogen bromide cleaves at methionine residues in proteins (Gross, E. (1967) Methods Enzymol. 11:238–255); hydroxylamine cleaves at Asn-Gly bonds (Bornstein, G. and Balian, G. (1970) J. Biol. Chem. 245: 4854–4856); and by hydrolysis at low pH (Asp-Pro bonds are labile at low pH) (Landon, M. (1977) Methods Enzymol 47(E):145–149.

Antibodies for Monitoring Peptide Treatment

The present invention provides a method of monitoring the peptide treatment of the present invention using antibodies raised against a peptide of the invention. An "antibody" in accordance with the present specification is defined broadly as a protein that binds specifically to an epitope. The antibody may be polyclonal or monoclonal. Antibodies further include recombinant polyclonal or monoclonal Fab fragments prepared in accordance with the method of Huse, et al. (1989) Science 246:1275–1281 and *Current Protocols in Immunology*, Coligan, J. et al. (Eds.), Wiley Intersciences (Eds.) NY (1999).

A. Preparing Antibodies

Polyclonal antibodies are isolated from mammals that have been inoculated with the peptide or a functional analog in accordance with methods known in the art *Current Protocols in Immunology*, Coligan, J., et al. (Eds.), Wiley Intersciences NY (1999).

The antibodies are preferably monoclonal. Monoclonal antibodies may be produced by methods known in the art. These methods include the immunological method described by Kohler and Milstein (1975) Nature 256:495–497 and by Campbell in "Monoclonal Antibody Technology, The Production and Characterization of Rodent and Human Hybridomas" in Burdon, et al. (Eds.) Laboratory Techniques in Biochemistry and Molecular Biology, Volume 13, Elsevier Science Publishers, Amsterdam (1985) and Coligan J., et al. (Eds.) *Current Protocols in Immunology*, Wiley Intersciences NY (1999); as well as the recombinant DNA method described by Huse, et al. (1989) Science 246:1275–1281.

The peptide may be conjugated to a carrier molecule to increase immunogenicity if desired. Some suitable carrier molecules include keyhold limpet hemocyanin and bovine serum albumen. Conjugation may be carried out by methods known in the art, such as those described in *Current Protocols in Immunology*, Coligan, J., et al. (Eds.) Chapter 9, Wiley Intersciences NY (1999). One such method is to combine a cysteine residue of the fragment with a cysteine residue on the carrier molecule.

B. Labeling Antibodies

The antibodies described above can be labeled in accordance with methods known in the art. Methods for labeling antibodies have been described, for example, by Hunter and Greenwood (1962) Nature 144:945 and by David, et al. (1974) Biochemistry 13: 1014–1021. Additional methods for labeling antibodies have been described in U.S. Pat. Nos. 3,940,475 and 3,645,090 and in *Using Antibodies, a Laboratory Manual*, Harlow, F. and Land E. (Eds.), Cold Spring Harbor Laboratory Press, Cold Spring Harbor, N.Y. (1999).

EXAMPLES

Example 1

Proliferative Response of Human Osteoblasts

The effect of the peptide (CGGGRWCG, Cys-Gly-Gly-Gly-Arg-Trp-Cys-Gly (SEQ. ID NO: 1)) on the stimulation of osteoblast proliferation was assessed in a short-term assay via measurement of the amount of the nucleotide thymidine that was incorporated into newly synthesized DNA.

Cys-Gly-Gly-Gly-Arg-Trp-Cys-Gly (SEQ. ID NO: 1) peptides were synthesized by Invitrogen Corporation (Carlsbad, Calif.).

Primary human osteoblasts were trypsinized and cell counts determined. Cells were resuspended at a concentration of $0.5 \times 10^5$ cells/ml in growth medium [Dulbeccos Modified Eagles Medium (DMEM) 10% Fetal Bovine Serum (FBS), 100 units Penicillin and 50 μg/ml Streptomycin]. A 100 μl aliquot of cells was added to each well in a 96 well dish. Cells were allowed to adhere for 24 hours and then refed with DMEM containing 0.5% FBS for 24 hours. Thereafter, several concentrations (10, 100, 500 μg/ml final concentration) of peptide in DMEM containing 0.5% FBS were added to different wells in quadruplicate. These plates were incubated in a cell culture incubator at 37° C. 5% $CO_2$ for 48 hours. Subsequently, 0.1 μCi of $^3$H-thymidine was added to each well, and incubated at 37° C. for an additional 3 hours prior to harvest. Cells were lysed and the lysate was placed in scintillation fluid and the amount of thymidine incorporated was determined by beta counting (in Counts Per Minute, or CPM). The results are shown in Table 1A.

TABLE 1A $^3$H-Thymidine Incorporation Into Osteoblasts

| Treatment | CPM |
| --- | --- |
| 0.1% BSA | 548 +/− 72 |
| CGGGRWCG (SEQ. ID NO: 1; 0 μg/ml) | 591 +/− 39 |
| CGGGRWCG (SEQ. ID NO: 1; 100 μg/ml) | 1228 +/− 157 |
| CGGGRWCG (SEQ. ID NO: 1; 500 μg/ml) | 629 +/− 46 |
| 10% FBS | 1931 +/− 71 |

The results in Table 1A show that 100 μg/ml of the peptide stimulated proliferation of osteoblasts. There was a 2.5 fold stimulation of proliferation as compared to controls treated with 0.1% BSA. At 500 μg/ml of the peptide, no statistical stimulation was observed.

To help determine a maximal stimulation of cell proliferation, the study was repeated with concentrations of 10, 50, 100, and 200 μg/ml final concentration) of the peptide represented by SEQ. ID NO: 1 in DMEM containing 0.5% FBS. The beta counting results are shown in Table 1B.

TABLE 1B $^3$H-Thymidine Incorporation Into Osteoblasts

| Treatment | CPM |
| --- | --- |
| 0.1% BSA | 784 +/− 59 |
| CGGGRWCG (SEQ. ID NO: 1; 10 μg/ml) | 807 +/− 45 |
| CGGGRWCG (SEQ. ID NO: 1; 50 μg/ml) | 948 +/− 62 |
| CGGGRWCG (SEQ. ID NO: 1; 100 μg/ml) | 1150 +/− 37 |
| CGGGRWCG (SEQ. ID NO: 1; 200 μg/ml) | 1565 +/− 98 |
| 10% FBS | 2088 +/− 154 |

The results in Table 1B show that the stimulation of proliferation was dose dependant, showing a maximal stimulation at 200 μg/ml. The stimulation of proliferation was approximately 75% of that observed when cells were cultured in the presence of serum.

Example 2

Proliferative Response of Human Osteoblasts Treated with Peptide (SEQ. ID NO: 1) versus BMP-2

Experiments were performed comparing the stimulatory effect of the CGGGRWCG peptide (SEQ. ID NO: 1) to BMP-2. The experiments were set up as described for Example 1, with proliferation assessed by measurement of thymidine incorporation into newly synthesized DNA. Following serum starvation, cells were treated with either the peptide or BMP-2 in DMEM containing 0.5% FBS. These plates were incubated at 37° C. in 5% $CO_2$ for 48 hours and processed for analysis as mentioned in Example 1. The results are shown in Table 2.

TABLE 2

$^3$H-Thymidine Incorporation Into Osteoblasts

| Treatment | CPM |
|---|---|
| 0.1% BSA | 1548 +/− 198 |
| CGGGRWCG (SEQ. ID NO: 1; 200 ug/ml) | 3446 +/− 333 |
| BMP-2, 10 ng/ml | 4232 +/− 155 |
| 10% FBS | 6640 +/− 223 |

Table 2 shows that osteoblast proliferation was stimulated two fold and was similar to that observed with BMP-2.

Example 3

Proliferative Response of Human Chondrocytes Treated with Peptide

The effect of the peptide CGGGRWCG (SEQ. ID NO: 1) on stimulation of human chondrocyte proliferation was assessed by thymidine incorporation as described above. The experiments were set up as detailed in Example 1. Following serum starvation, cells were treated with the peptide at concentration of 10, 100, and 500 μg/ml of peptide in DMEM containing 0.5% FBS. These plates were incubated at 37° C. in 5% $CO_2$ for 48 hours and processed for analysis as described in Example 1. The results are shown in Table 3.

TABLE 3

$^3$H-Thymidine Incorporation Into Chondrocytes

| Treatment | CPM |
|---|---|
| 0.1% BSA | 632 +/− 61 |
| CGGGRWCG (SEQ. ID NO: 1; 10 μg/ml) | 803 +/− 96 |
| CGGGRWCG (SEQ. ID NO: 1; 100 μg/ml) | 726 +/− 88 |
| CGGGRWCG (SEQ. ID NO: 1; 500 μg/ml) | 640 +/− 80 |
| 10% FBS | 1594 +/− 214 |

Table 3 shows that the peptide did not stimulate proliferation of human chondrocytes at the concentrations tested.

Example 4

Proliferative Response of Human Fibroblasts Treated with Peptide (SEQ. ID NO: 1)

The effect of the peptide CGGGRWCG (SEQ. ID NO: 1) on stimulation of human fibroblast proliferation was assessed by thymidine incorporation as described above. The experiments were set up as detailed in Example 1. Following serum starvation, cells were treated with the peptide at concentration of 10, 100, and 500 μg/ml of peptide in DMEM containing 0.5% FBS. These plates were incubated at 37° C. in 5% $CO_2$ for 48 hours and processed for analysis as described in Example 1. The results are shown in Table 4.

TABLE 4

$^3$H-Thymidine Incorporation Into Chondrocytes

| Treatment | CPM |
|---|---|
| 0.1% BSA | 1115 +/− 150 |
| CGGGRWCG (SEQ. ID NO: 1; 10 μg/ml) | 1281 +/− 86 |
| CGGGRWCG (SEQ. ID NO: 1; 100 μg/ml) | 1103 +/− 76 |
| CGGGRWCG (SEQ. ID NO: 1; 500 μg/ml) | 1088 +/− 64 |
| 10% FBS | 5154 +/− 141 |

Table 4 shows that the peptide did not stimulate proliferation of human fibroblasts at the concentrations tested.

Example 5

Formation of Inter-chain Disulfide Bonds

The formation of inter- or intra-chain disulfide bonds was determined by Elman's test and a reverse phase HPLC method. The peptide represented by SEQ. ID NO: 1 was dissolved in 50 mM sodium acetate, pH 5.2, containing 1 mM EDTA to a stock solution of 10 mM. The stock solution was further diluted with either 50 mM sodium acetate buffer or Elman's reaction buffer (0.1 mM sodium phosphate, pH 8.0, containing 1 mM EDTA) to a final concentration of 0.5 mM. Samples prepared with sodium acetate buffer were kept at 5° C. for HPLC analysis later.

The reagent used in Elman's test is 5,5'-dithio-bis-(2-nitrobenzoic acid), also know as DTNB. DTNB reacts with a free sulfhydryl group to yield a mixed disulfide and 2-nitro-5-thiobenzoic acid (TNB), resulted in color formation. Sulfhydryl groups can be quantitated in a sample by comparison to a standard curve prepared with know concentrations of sulfhydryl-containing compound such as cysteine. The measurement of free sulfhydryl group was performed when the peptide was freshly prepared and after 24 hours incubation at 37° C. The incubation step was designed to mimic the cell culture conditions and to create conditions for inter- or intra-chain disulfide bond formations. To examine the integrity of the peptide after incubation, a UV measurement was performed when the peptide (SEQ. ID NO: 1) was freshly prepared and after 24 hours incubation. The results are shown in Table 5.

TABLE 5

| Measurement of Free Sulfhydryl Group Content | | |
|---|---|---|
| | Optical density | |
| Samples | At 412 nM | At 280 nM |
| G1-Fresh | 0.71 | 2.127 |
| G1-24 hrs | 0.011 | 2.037 |

Table 5 shows absorbance of the peptide between freshly prepared and 24 hour old samples. The results of the peptide at 412 nM show that the free sulfhydryl group content in the peptide was reduced significantly after 24 hour incubation, an indication of disulfide bond formations. The absorbance of the peptide at 280 nM did not change.

To determine the integrity of the peptide of SEQ. ID NO: 1 after disulfide bond formations, samples in sodium acetate buffer (1G1) and in Elman's reaction buffer (1G2) were subjected to reverse phase HPLC after a 24 hour incubation at 37° C. In particular, a 0–80% acetonitrile gradient in 0.1%

TFA was used over 15 minutes at a flow rate of 2 ml/min on a Vydac C-18 column. Detection was at 214 nm. The results are shown in FIG. 1.

FIG. 1 shows that the peptide of SEQ. ID NO: 1 formed intra-chain disulfide bonds (ring structure) and not a higher lever structure in the reaction buffer (1G2) as evidenced by the peak at 5.4 min. The retention time of the peptide with free sulfhydryl groups was 5.7 min. Samples prepared in the sodium acetate buffer (1G1) included some disulfide bonds after 24 hours incubation as evidenced by the peak at 5.4 min, but predominately contained free sulfhydryl groups, as indicated by the peak at 5.7 min. FIG. 1 indicates that the peptide of SEQ. ID NO: 1 was intact after 24 hours incubation, because no major peaks other than the peaks at 5.4 min. and 5.7 min. were present.

What is claimed is:

1. An osteoinductive composition comprising an isolated or recombinant peptide component having the formula:

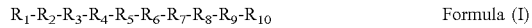

$$R_1\text{-}R_2\text{-}R_3\text{-}R_4\text{-}R_5\text{-}R_6\text{-}R_7\text{-}R_8\text{-}R_9\text{-}R_{10} \qquad \text{Formula (I)}$$

or a pharmaceutically acceptable salt thereof, wherein:

$R_1$ is H; formyl; mono- or di-lower (C1–C8 linear or branched) alkyl; aryl; lower (C1–C8 linear or branched) alkanoyl; aroyl; aroyl substituted with 1–3 substituents selected from the group consisting of fluorine, chlorine, bromine, C 1–C8 linear or branched alkyl, and C1–C8 linear or branched alkyloxy; C1–C8 linear or branched alkyloxycarbonyl; aryloxycarbonyl; or aryloxycarbonyl substituted with 1–3 substituents selected from the group consisting of fluorine, chlorine, bromine, C1–C8 linear or branched alkyl, and C1–C8 linear or branched alkyloxy;

$R_2$ and $R_8$ are each independently selected from D-cysteine, L-cysteine, D-homocysteine, L-homocysteine, D-penicillamine, or L-penicillamine;

$R_3$, $R_4$ and $R_5$ are each glycine; or $R_3$ and $R_4$ taken together are δ-amino-pentanoic acid; or $R_4$ and $R_5$ taken together are δ-amino-pentanoic acid;

$R_6$ is arginine or homo-arginine;

$R_7$ is tryptophan;

$R_9$ is glycine; and $R_{10}$ is OH, C1–C8 linear or branched alkyl ester, lower aryl ester, or $NR_{11}R_{12}$ where $R_{11}$ and $R_{12}$ are each selected independently from H, C1–C8 linear or branched alkyl, or aryl.

2. The composition of claim 1, wherein the peptide component has the amino acid sequence of SEQ. ID NO:1.

3. The composition of claim 2, wherein the peptide component is part of a longer peptide or polypeptide.

4. The composition of claim 1, wherein said peptide component includes intra-chain disulfide bonds.

5. The composition of claim 1, wherein said peptide component forms inter-chain disulfide bonds with others of said peptide component.

6. The composition of claim 5, comprising a homodimer of said peptide component.

7. The composition of claim 1, further comprising osteoprogenitor stem cells and/or osteoblasts.

8. The composition of claim 1, further comprising a pharmaceutically acceptable carrier or aqueous solvent.

9. The composition of claim 1, further including an additive selected from the group consisting of stabilizer, preservative, thickener, solubilizer and combinations thereof.

10. The composition of claim 1, further including osteoinductive factors selected from the group consisting of dexamethasone, ascorbic acid-2-phosphate, beta-glycerophosphate, and combinations thereof.

11. The composition of claim 1, further including an agent selected from the group consisting of antibiotics, antimycotics, anti-inflammatory drugs, immunosuppressive drugs, and combinations thereof.

12. The composition of claim 1, further including an osteoinductive substance selected from the group consisting of growth factors, cytokines, hormones, enzymes, enzyme inhibitors, bone matrix components, growth differentiation factors and combinations thereof.

13. The composition of claim 12, wherein the growth factor is selected from the group consisting of epidermal growth factor, platelet-derived growth factor, members of the transforming growth factor superfamily of proteins, insulin-like growth factor, basic fibroblast growth factor, bone morphogenic proteins and combinations thereof.

14. The composition of claim 1, further comprising a delivery vehicle for said peptide component, said delivery vehicle being a bone-compatible matrix.

15. The composition of claim 1, further comprising osteoprogenitor stem cells and/or osteoblasts.

16. The composition of claim 14, wherein said bone-compatible matrix provides for slow release of said peptide component to a patient in need of said composition and/or provides a structure for developing bone in the patient.

17. The composition of claim 14, wherein said peptide component is immobilized to, or encapsulated or impregnated within said bone-compatible matrix.

18. The composition of claim 14, wherein said bone-compatible matrix is a porous structure.

19. The composition of claim 14, wherein said bone-compatible matrix is in a form selected from the group consisting of powder, microparticles, microspheres, microfibers, microfibrils, strip, gel, web, sponge and combinations thereof.

20. The composition of claim 14, wherein said bone-compatible matrix is a ceramic.

21. The composition of claim 20, wherein said ceramic is a three-dimensional scaffold.

22. The composition of claim 20, wherein said ceramic is selected from the group consisting of calcium sulfate, hydroxyapatite, tricalcium phosphate and combinations thereof.

23. The composition of claim 14, wherein said bone-compatible matrix is demineralized bone matrix.

24. The composition of claim 14, wherein said bone-compatible matrix is selected from the group consisting of natural biodegradable polymer, modified natural biodegradable polymer, synthetic biodegradable polymer and combinations thereof.

25. The composition of claim 24, wherein said polymer is selected from the group consisting of fibrin, collagen, elastin, celluloses, gelatin, vitronectin, fibronectin, laminin, reconstituted basement membrane matrices, starches, dextrans, alginates, hyaluron, chitin, chitosan, agarose, polysaccharides, hyaluronic acid, poly(lactic acid), poly(glycolic acid), polyethylene glycol, decellularized tissue, self-assembling peptides, polypeptides, glycosaminoglycans, their derivatives and mixtures thereof.

26. The composition of claim 24, wherein said polymer is selected from the group consisting of polydioxanones, polycarbonates, polyoxalates, poly(α-esters), polyanhydrides, polyacetates, polycaprolactones, poly(orthoesters), polyamino acids, polyamides and mixtures and copolymers thereof.

27. The composition of claim 24, wherein said polymer is selected from the group consisting of stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and poly(lactic acid), copolymers of α-amino acids, copolymers of α-amino acids and caproic acid, copolymers of α-benzyl glutamate and polyethylene glycol, copolymers of succinate and poly(glycols), polyphosphazene, polyhydroxy-alkanoates and mixtures thereof.

28. The composition of claim 24, wherein said polymer is a synthetic hydrogel polymer.

29. The composition of claim 24, wherein said peptide component is controllably released from said biodegradable polymer to the site where it is needed by hydrolysis of chemical bonds in said biodegradable polymer.

30. An osteoinductive implant comprising:
a bone-compatible matrix; and
a peptide component associated with said bone-compatible matrix, the peptide component having the formula:

$$R_1-R_2-R_3-R_4-R_5-R_6-R_7-R_8-R_9-R_{10} \qquad \text{Formula (I)}$$

or a pharmaceutically acceptable salt thereof, wherein:

$R_1$ is H; formyl; mono- or di-lower (C1–C8 linear or branched) alkyl; aryl; lower (C1–C8 linear or branched) alkanoyl; aroyl; aroyl substituted with 1–3 substituents selected from the group consisting of fluorine, chlorine, bromine, C1–C8 linear or branched alkyl, and C1–C8 linear or branched alkyloxy; C1–C8 linear or branched alkyloxycarbonyl; aryloxycarbonyl; or aryloxycarbonyl substituted with 1–3 substituents selected from the group consisting of fluorine, chlorine, bromine, C1–C8 linear or branched alkyl, and C1–C8 linear or branched alkyloxy;

$R_2$ and $R_8$ are each independently selected from D-cysteine, L-cysteine, D-homocysteine, L-homocysteine, D-penicillamine, or L-penicillamine;

$R_3$, $R_4$ and $R_5$ are each glycine; or $R_3$ and $R_4$ taken together are δ-amino-pentanoic acid; or $R_4$ and $R_5$ taken together are δ-amino-pentanoic acid;

$R_6$ is arginine or homo-arginine;

$R_7$ is tryptophan;

$R_9$ is glycine; and $R_{10}$ is OH, C1–C8 linear or branched alkyl ester, lower aryl ester, or $NR_{11}R_{12}$ where $R_{11}$ and $R_{12}$ are each selected independently from H, C1–C8 linear or branched alkyl, or aryl.

31. The implant of claim 30, further comprising osteoprogenitor stem cells and/or osteoblasts associated with said bone-compatible matrix.

32. The implant of claim 30, wherein the peptide component has the amino acid sequence of SEQ. ID NO:1.

33. The implant of claim 30, wherein the peptide component is immobilized to said bone-compatible matrix.

34. The implant of claim 30, wherein the peptide component is impregnated or encapsulated within said bone-compatible matrix.

35. The implant of claim 30, wherein said bone-compatible matrix is selected from the group consisting of biodegradable polymer, demineralized bone matrix, ceramic and combinations thereof.

36. A treatment method for promoting proliferation of osteoblasts comprising administering to a patient in need of such treatment an osteoinductive composition comprising an isolated or recombinant peptide component having the formula:

$$R_1-R_2-R_3-R_4-R_5-R_6-R_7-R_8-R_9-R_{10} \qquad \text{Formula (I)}$$

or a pharmaceutically acceptable salt thereof, wherein:

$R_1$ is H; formyl; mono- or di-lower (C1–C8 linear or branched) alkyl; aryl; lower (C1–C8 linear or branched) alkanoyl; aroyl; aroyl substituted with 1–3 substituents selected from the group consisting of fluorine, chlorine, bromine, C1–C8 linear or branched alkyl, and C1–C8 linear or branched alkyloxy; C1–C8 linear or branched alkyloxycarbonyl; aryloxycarbonyl; or aryloxycarbonyl substituted with 1–3 substituents selected from the group consisting of fluorine, chlorine, bromine, C1–C8 linear or branched alkyl, and C1–C8 linear or branched alkyloxy;

$R_2$ and $R_8$ are each independently selected from D-cysteine, L-cysteine, D-homocysteine, L-homocysteine, D-penicillamine, or L-penicillamine;

$R_3$, $R_4$ and $R_5$ are each glycine; or $R_3$ and $R_4$ taken together are δ-amino-pentanoic acid; or $R_4$ and $R_5$ taken together are δ-amino-pentanoic acid;

$R_6$ is arginine or homo-arginine;

$R_7$ is tryptophan;

$R_9$ is glycine; and $R_{10}$ is OH, C1–C8 linear or branched alkyl ester, lower aryl ester, or $NR_{11}R_{12}$ where $R_{11}$ and $R_{12}$ are each selected independently from H, C1–C8 linear or branched alkyl, or aryl.

37. The method of claim 36, wherein the peptide component has the amino acid sequence of SEQ. ID NO:1.

38. The method of claim 36, wherein the composition administered comprises a homodimer of said peptide component.

39. The method of claim 36, wherein the composition administered further comprises osteoprogenitor stem cells and/or osteoblasts.

40. The method of claim 36, wherein the composition administered further comprises a pharmaceutically acceptable carrier or aqueous solvent.

41. The method of claim 36, wherein the composition administered further comprises a delivery vehicle for said peptide component, said delivery vehicle being a bone-compatible matrix which provides for slow release of said peptide component to a patient in need of said composition.

42. The method of claim 36, wherein said bone-compatible matrix is selected from the group consisting of biodegradable polymer, demineralized bone matrix, ceramic and combinations thereof.

43. The method of claim 36, wherein the composition is administered locally as an implant or device, topically or systemically.

44. The method of claim 36, wherein the treatment is useful for treating bone fractures.

45. The method of claim 36, wherein the treatment is useful for treating diseases or anomalies associated with deficient sites of bone.

46. The method of claim 45, wherein said diseases are selected from the group consisting of rheumatoid arthritis and osteoporosis.

47. The method of claim 45, wherein said anomalies are selected from the group consisting of craniofacial anomalies, dental anomalies and periodontal anomalies.

48. The method of claim 36, further comprising the step of monitoring the treatment with an antibody against the peptide component or a fragment thereof.

49. A method of preparing an osteoinductive composition comprising combining a bone-compatible matrix with a peptide component; and immobilizing said peptide component to or within said bone-compatible matrix, the peptide component having the formula:

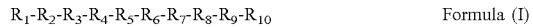   Formula (I)

or a pharmaceutically acceptable salt thereof, wherein:

$R_1$ is H; formyl; mono- or di-lower (C1–C8 linear or branched) alkyl; aryl; lower (C1–C8 linear or branched) alkanoyl; aroyl; aroyl substituted with 1–3 substituents selected from the group consisting of fluorine, chlorine, bromine, C1–C8 linear or branched alkyl, and C1–C8 linear or branched alkyloxy; C1–C8 linear or branched alkyloxycarbonyl; aryloxycarbonyl; or aryloxycarbonyl substituted with 1–3 substituents selected from the group consisting of fluorine, chlorine, bromine, C1–C8 linear or branched alkyl, and C1–C8 linear or branched alkyloxy;

$R_2$ and $R_8$ are each independently selected from D-cysteine, L-cysteine, D-homocysteine, L-homocysteine, D-penicillamine, or L-penicillamine;

$R_3$, $R_4$ and $R_5$ are each glycine; or $R_3$ and $R_4$ taken together are δ-amino-pentanoic acid; or $R_4$ and $R_5$ taken together are δ-amino-pentanoic acid;

$R_6$ is arginine or homo-arginine;

$R_7$ is tryptophan;

$R_9$ is glycine; and $R_{10}$ is OH, C1–C8 linear or branched alkyl ester, lower aryl ester, or $NR_{11}R_{12}$ where $R_{11}$ and $R_{12}$ are each selected independently from H, C1–C8 linear or branched alkyl, or aryl.

50. The method of claim 49, further comprising the step of combining said osteoinductive composition with osteoprogenitor stem cells and/or osteoblasts.

51. The method of claim 50, further comprising impregnating or encapsulating said cells within said bone-compatible matrix.

52. The method of claim 49, wherein the peptide component has the amino acid sequence of SEQ. ID NO:1.

53. A composition comprising the reaction product of (i) a bone-compatible matrix; (ii) osteoinductive cells; and (iii) a peptide component having the formula:

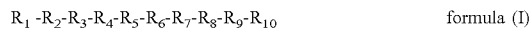   formula (I)

or a pharmaceutically acceptable salt thereof, wherein:

$R_1$ is H; formyl; mono- or di-lower (C1–C8 linear or branched) alkyl; aryl; lower (C1–C8 linear or branched) alkanoyl; aroyl; aroyl substituted with 1–3 substituents selected from a the group consisting of fluorine, chlorine, bromine, C1–C8 linear or branched alkyl, and C1–C8 linear or branched alkyloxy; C1–C8 linear or branched alkyloxycarbonyl, aryloxycarbonyl or aryloxycarbonyl substituted with 1–3 substituents selected from the group consisting of fluorine, chlorine, bromine, C1–C8 linear or branched alkyl, and C1–C8 linear or branched alkyloxy;

$R_2$ and $R_8$ are each independently selected from D-cysteine, L-cysteine, D-homocysteine, L-homocysteine, D-penicillamine, or L-penicillamine;

$R_3$, $R_4$ and $R_5$ are each glycine; or $R_3$ and $R_4$ taken together are δ-amino-pentanoic acid; or $R_4$ and $R_5$ taken together are δ-amino-pentanoic acid;

$R_6$ is arginine or homo-arginine;

$R_7$ is tryptophan;

$R_9$ is glycine; and $R_{10}$ is OH, C1–C8–C8 linear or branched alkyl ester, lower aryl ester, or $NR_{11}R_{12}$ where $R_{11}$ and $R_{12}$ are each selected independently from H, C1–C8 linear or branched alkyl, or aryl.

54. The composition of claim 53, wherein the peptide component has the amino acid sequence of SEQ. ID NO: 1.

55. A kit including one or more containers comprising:
(i) a material selected from the group consisting of (a) bone-compatible matrix, (b) carrier or aqueous solvent, (c) stabilizer, (d) preservative, (e) thickener, (f) solubilizer, and (g) cells capable of forming bone; and
(ii) one or more containers comprising a peptide component having the formula:

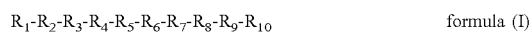   formula (I)

or a pharmaceutically acceptable salt thereof, wherein:

$R_1$ is H; formyl; mono- or di-lower (C1–C8 linear or branched) alkyl; aryl; lower (C1–C8 linear or branched) alkanoyl; aroyl; aroyl substituted with 1–3 substituents selected from a the group consisting of fluorine, chlorine, bromine, C1–C8 linear or branched alkyl, and C1–C8 linear or branched alkyloxy; C1–C8 linear or branched alkyloxycarbonyl, aryloxycarbonyl or aryloxycarbonyl substituted with 1–3 substituents selected from the group consisting of fluorine, chlorine, bromine, C1–C8 linear or branched alkyl, and C1–C8 linear or branched alkyloxy;

$R_2$ and $R_8$ are each independently selected from D-cysteine, L-cysteine, D-homocysteine, L-homocysteine, D-penicillamine, or L-penicillamine;

$R_3$, $R_4$ and $R_5$ are each glycine; or $R_3$ and $R_4$ taken together are δ-amino-pentanoic acid; or $R_4$ and $R_5$ taken together are δ-amino-pentanoic acid;

$R_6$ is arginine or homo-arginine;

$R_7$ is tryptophan;

$R_9$ is glycine; and $R_{10}$ is OH, C1–C8 linear or branched alkyl ester, lower aryl ester, or $NR_{11}R_{12}$ where $R_{11}$ and $R_{12}$ are each selected independently from H, C1–C8 linear or branched alkyl, or aryl.

56. The kit of claim 55, wherein the peptide component has the amino acid sequence of SEQ. ID NO:1.

57. An isolated or recombinant peptide having SEQ. ID NO: 1.

58. The implant of claim 30, wherein the peptide component is part of a longer peptide or polypeptide.

59. The method of claim 36, wherein the peptide component is part of a longer peptide or polypeptide.

60. The method of claim 49, wherein the peptide component is part of a longer peptide or polypeptide.

61. The composition of claim 53, wherein the peptide component is part of a longer peptide or polypeptide.

62. The kit of claim 55, wherein the peptide component is part of a longer peptide or polypeptide.

* * * * *

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: synthesized primer

<400> SEQUENCE: 1

Cys Gly Gly Gly Arg Trp Cys Gly
1               5